(12) United States Patent
Abehasera et al.

(10) Patent No.: US 11,235,079 B1
(45) Date of Patent: Feb. 1, 2022

(54) UVC GERMICIDAL LIGHT FOR INDOOR APPLIANCES

(71) Applicant: UV 426 LLC, Hallandale, FL (US)

(72) Inventors: Benyamin Abehasera, Hallandale Beach, FL (US); Zohar Pinhasi, Hollywood, FL (US)

(73) Assignee: UV 426, LLC, Hollywood, FL (US)

( * ) Notice: Subject to any disclaimer, the term of this patent is extended or adjusted under 35 U.S.C. 154(b) by 0 days.

(21) Appl. No.: 17/010,475

(22) Filed: Sep. 2, 2020

(51) Int. Cl.
*A61L 2/10* (2006.01)
*A61L 2/24* (2006.01)
*A61L 2/08* (2006.01)
*A61L 2/26* (2006.01)

(52) U.S. Cl.
CPC .............. *A61L 2/084* (2013.01); *A61L 2/24* (2013.01); *A61L 2/26* (2013.01); *A61L 2202/11* (2013.01); *A61L 2202/14* (2013.01)

(58) Field of Classification Search
CPC .......... A61L 2/10; A61L 2/24; A61L 2202/11; A61L 2202/14
See application file for complete search history.

(56) References Cited

U.S. PATENT DOCUMENTS

| | | | | |
|---|---|---|---|---|
| 2011/0038754 | A1* | 2/2011 | James | C02F 1/325 422/24 |
| 2013/0117936 | A1* | 5/2013 | Stryker | A61G 7/05 5/600 |
| 2016/0296649 | A1* | 10/2016 | Ramanand | A61L 2/10 |
| 2016/0324996 | A1* | 11/2016 | Bilenko | A61L 2/24 |

\* cited by examiner

*Primary Examiner* — Kevin Joyner
(74) *Attorney, Agent, or Firm* — Berger Singerman LLP; Geoffrey Lottenberg

(57) ABSTRACT

A UVC germicidal light for indoor appliances includes a housing having UVC LED light strips, a power source, an on-off switch and an LED frequency and amplitude adjustment circuit. The light includes a magnetic attachment so that the unit can be placed inside an appliance such as a washer, dryer, dishwasher, refrigerator, or the like. Multiple modes of operation, including dimming, allow the user to select the ideal conditions for the application and germicidal needs. The UVC LEDs are configured to emit light in the range of 200-280 nm.

15 Claims, 3 Drawing Sheets

UVC GERMICIDAL LIGHT FOR INDOOR APPLIANCES

CROSS REFERENCE TO RELATED APPLICATIONS

N/A

It will be recognized that some or all of the figures are schematic representations for purposes of illustration and do not necessarily depict the actual relative sizes or locations of the elements shown. The figures are provided for the purpose of illustrating one or more embodiments of the invention with the explicit understanding that they will not be used to limit the scope or the meaning of the claims.

DETAILED DESCRIPTION OF THE INVENTION

In the following description, for the purposes of explanation, numerous specific details are set forth in order to provide a thorough understanding of the invention. It will be apparent, however, to one skilled in the art that the invention may be practiced without some of these specific details. Throughout this description, the embodiments and examples shown should be considered as exemplars, rather than as limitations on the invention. That is, the following description provides examples, and the accompanying drawings show various examples for the purposes of illustration. However, these examples should not be construed in a limiting sense as they are merely intended to provide examples of the invention rather than to provide an exhaustive list of all possible implementations of thereof.

Specific embodiments of the invention will now be further described by the following, non-limiting examples which will serve to illustrate various features. The examples are intended merely to facilitate an understanding of ways in which the invention may be practiced and to further enable those of skill in the art to practice the invention. Accordingly, the examples should not be construed as limiting the scope of the invention. In addition, reference throughout this specification to "one embodiment" or "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment. Furthermore, the particular features, structures or characteristics may be combined in any suitable manner in one or more embodiments.

Figure 1A:
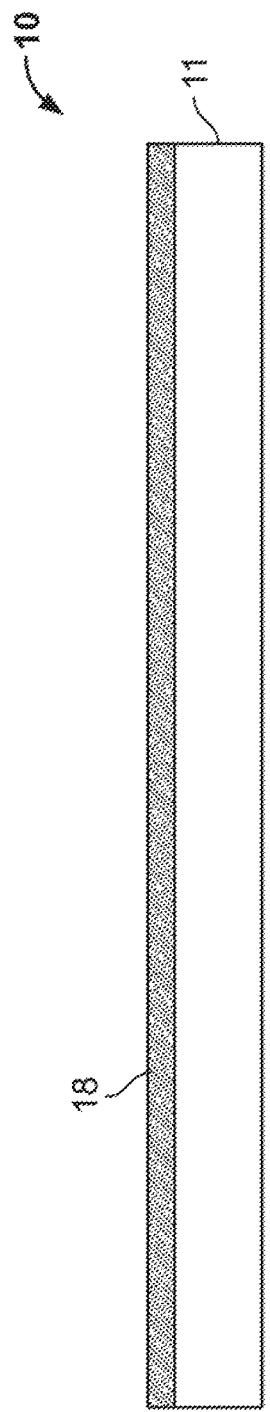
FIG. 1A is a top view of the germicidal light.
Figure 1B:
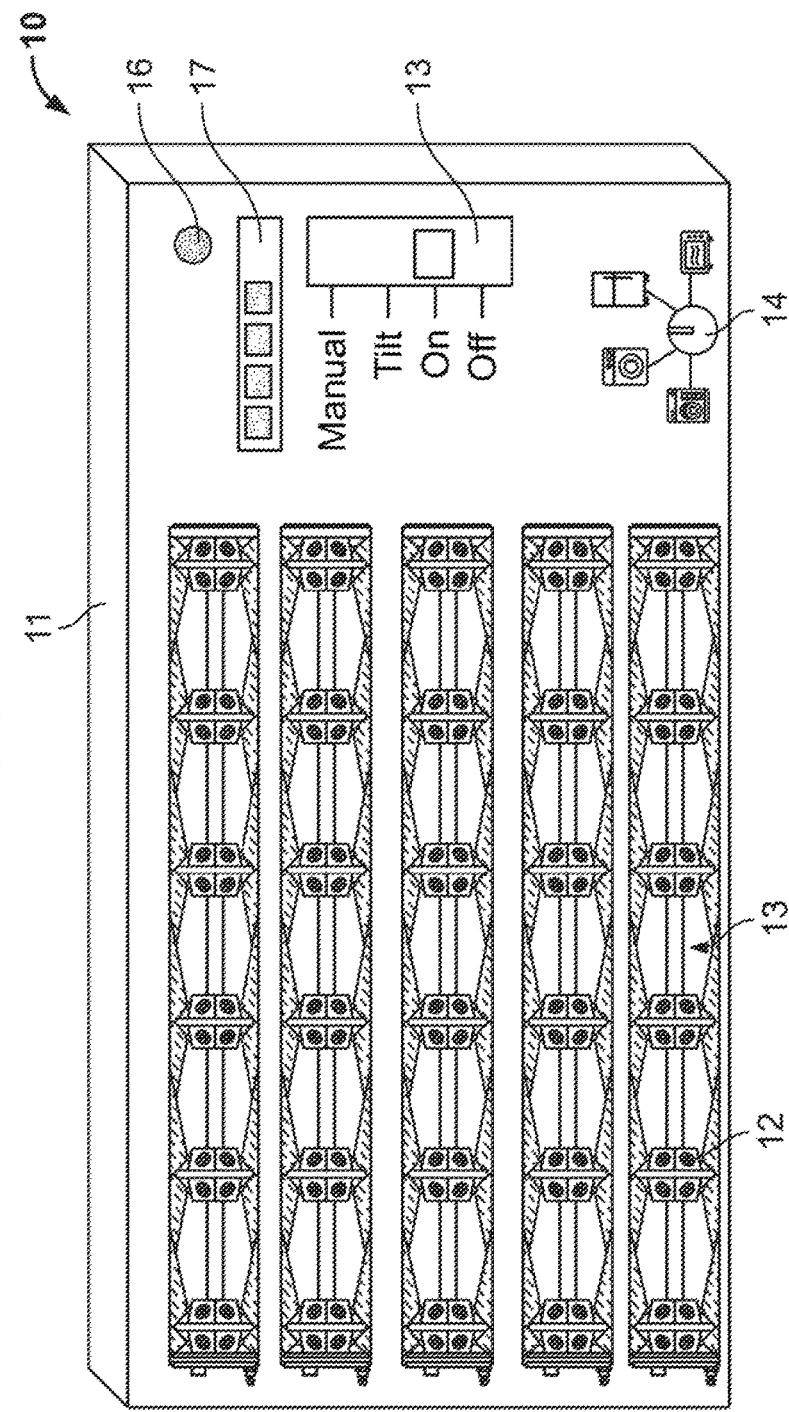
FIG. 1B is a front view of the germicidal light.

Referring to FIGS. 1A and 1B, shown is a UVC light system 10 comprising a housing 11 and one or more LED lights 12. In some embodiments, the LED lights are configured in LED strips 13 wherein a plurality of LED strips 13 can be arranged adjacent to one another to form an array of LED lights. The housing includes an power source such as a rechargeable battery, which can be recharged via universal serial bus (USB) or other power adapter connections. The light system 10 also includes one or more controls including an mode selector switch 14 and a preset switch 15. Also included are one or more indicators including an on/off indicator 16 and a battery level indicator 17. In some embodiments, the rear of the housing 11 includes one or more magnets 18 that are used to attach the housing 11 to a magnetically charged surface, such as the metal surface of the inside of an appliance. Other fasteners may employed, such as suction cups, screws, nails, double-sided tape, the like to allow the housing 11 to be affixed to a surface.

The LED lights 12 can be configured to emit light in variety of visible and non-visible light wavelength ranges. In some embodiments, the LED lights 12 are configured to emit light of a wavelength in the range of 100-280 nm and, more particularly, in the range of 200-280 nm, which is considered the UVC range effective for killing microorganisms such as bacteria, viruses, and the like.

Figure 2:
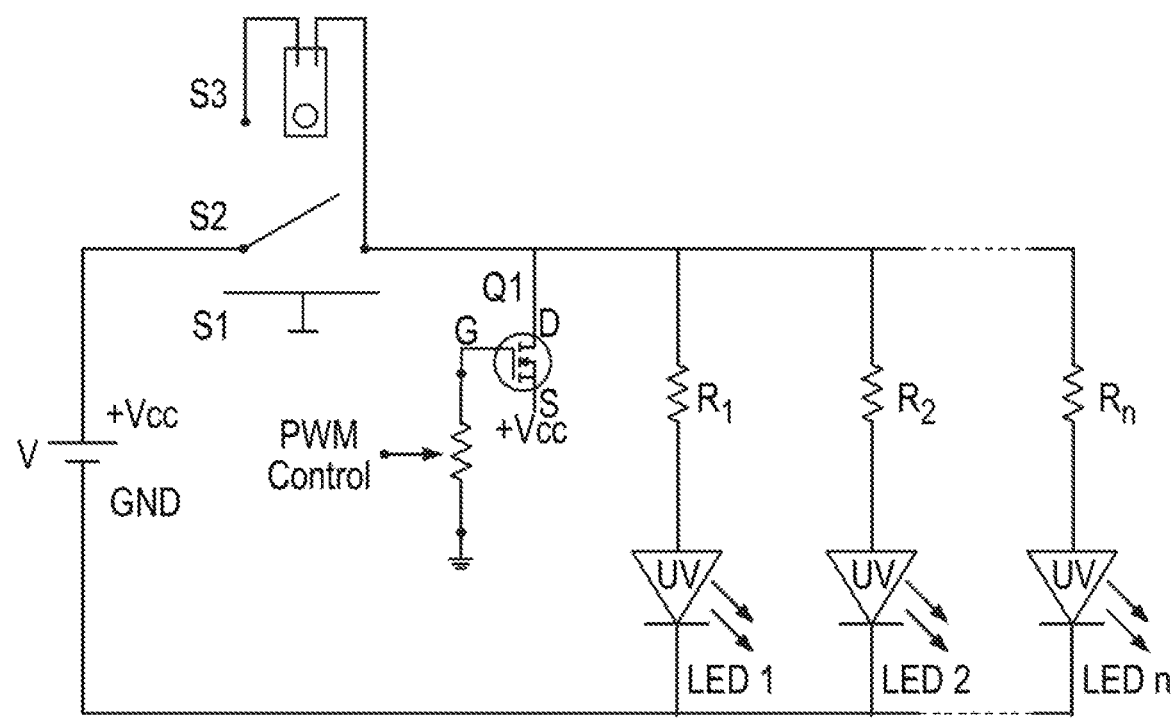
FIG. 2 is a circuit diagram of the LED frequency and amplitude adjustment circuit.
Figure 3:
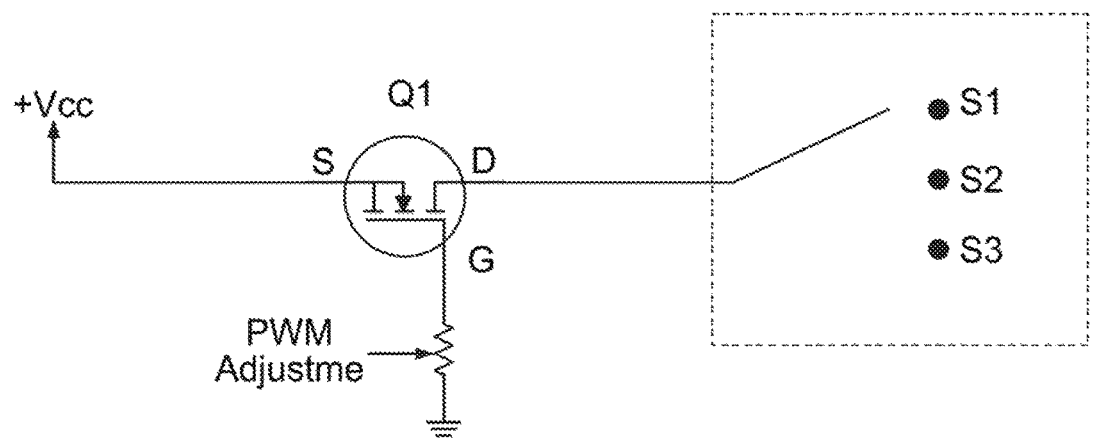
FIG. 3 is a circuit diagram of a the mode control circuit.

With reference to FIG. 2, shows in an LED frequency and amplitude adjustment circuit 20, which is controlled by the mode selector switch 14 and/or the preset switch 15. The circuit 20 includes a momentary switch S1, an on/off or latch switch S2, and a tilt/ball switch S3. The circuit also comprises a MOSFET Q1 which is used to adjust and control the voltage, frequency, amplitude and interval of the pulse width modulation (PWM) (dimming) of the LED lights 12. Shown also are LED 1, LED 2, and LED n, which represent the one or more LED lights 12 used in the light system. FIG. 3 shows the mode circuit 30 with elements corresponding to the circuit elements shown in FIG. 2. The mode circuit 30 is controlled by the user via mode switch 14. The mode circuit 30 provides three modes of operation, when the switch S1 is selected, the mode is "momentary" whereby the LED lights 12 are turned on so long as the switch S1 is pressed down. Switch S2 is an on/off toggle whereby the LED lights 12 are on when the switch S2 is in the on position, i.e. latch switching. Switch S3 is a tilt or rocker switch which turns on the LED lights 12 when the switch S3 is tilted toward the on position. In some embodiments, MOSFET Q1 is controlled by present switch 15 which allows the user to control the pulse width modulation (dimming), voltage, frequency, and amplitude of the LED lights 12.

Figure 4:
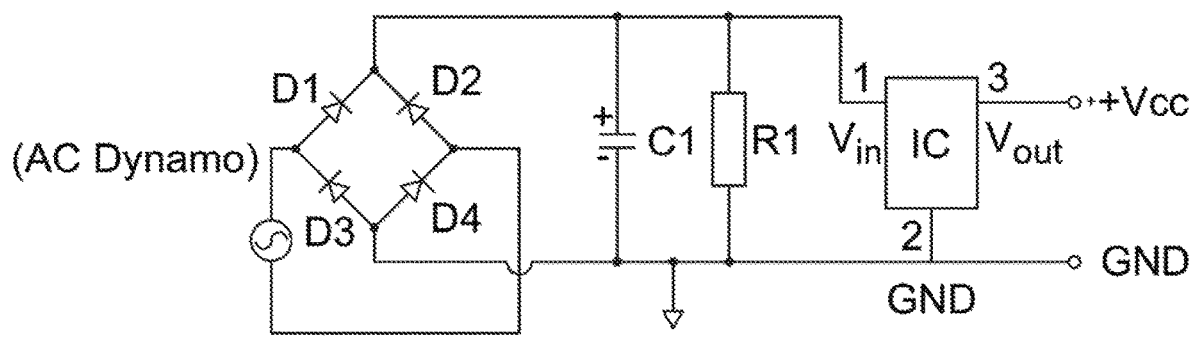
FIG. 4 is a circuit diagram of an AC dynamo circuit.

In some embodiments, the light system 10 receives power from power source such as a rechargeable battery, AC power source or the like. In some embodiments, the power source can comprise or be supplemented by an air-flow powered dynamo-type power supply, an exemplary circuit of which is shown in FIG. 4. The dynamo power supply circuit is connected to a rotating element of the appliance in which it is used, such as the drum of a spinning washer or dryer, whereby the rotating action of the appliance rotates the dynamo, which dynamo generates a voltage differential in responds to the changing magnetic field that results from rotation of the dynamo. In one example, the dynamo-type power supply is configured to generate 5V, which is sufficient to power the LED lights 12 described herein. In some embodiments, the dynamo circuit can be used to re-charge the rechargeable battery of the unit, rather than, or supplement to, the dynamo circuit providing power directly to the LED lights 12.

It is appreciated and understood that the light system 10 provides a germicidal LED light system for installation, removable or otherwise, inside an appliance such as a washer, dryer, refrigerator, dishwasher or the like. Given that in some embodiments the light system 10 is battery-powered, the system does not require an external power cabling to pass through the appliance within which the system 10 is installed. The mode and preset switching provides the user with variety of operation to address desired disinfection and sanitation needs based on the size, shape, load, and other configurations of the application. The use of UVC light emission in a desired range for a predetermine period of disinfection provides ideal sanitation and germicidal conditions to reduce and/or eliminate pathogens such as viruses and bacteria that may be present inside the appliance.

In some embodiments, the light system 12 can include a microprocessor in electronic communication with the power source and control circuits described herein. In some embodiments the microprocessor includes a communications radio such as WiFi, Bluetooth, NFC or the like that allows the light system 12 to communicate with and be controlled by an external controller such as a smartphone or other computing device, through for example a software mobile application. This processing system can comprise a microprocessor and other circuitry that retrieves and executes software from a storage system. The processing system can be implemented within a single processing device but can also be distributed across multiple processing devices or sub-systems that cooperate in executing program instructions. Examples of processing system include general purpose central processing units, application specific processors, and logic devices, as well as any other type of processing device, combinations of processing devices, or variations thereof. The storage system can comprise any storage media readable by processing system, and capable of storing software. The storage system can include volatile and nonvolatile, removable and non-removable media implemented in any method or technology for storage of information, such as computer readable instructions, data structures, program modules, or other data. The storage system can be implemented as a single storage device but may also be implemented across multiple storage devices or sub-systems. The storage system can comprise additional elements, such as a controller, capable of communicating with processing system.

Examples of storage media include random access memory, read only memory, magnetic disks, optical disks, flash memory, virtual memory, and non-virtual memory, magnetic cassettes, magnetic tape, magnetic disk storage or other magnetic storage devices, or any other medium which can be used to store the desired information and that may be accessed by an instruction execution system, as well as any combination or variation thereof, or any other type of storage media. In some implementations, the storage media can be a non-transitory storage media. In some implementations, at least a portion of the storage media may be transitory. It should be understood that in no case is the storage media a propagated signal. Although one software module is shown, the software may be distributed across many devices, storage media, etc.

It is to be noticed that the term "comprising," used in the claims, should not be interpreted as being limitative to the means listed thereafter. Thus, the scope of the expression "a device comprising means A and B" should not be limited to devices consisting only of components A and B. It means that with respect to the present invention, the only relevant components of the device are A and B. Put differently, the terms "including", "comprising" and variations thereof mean "including but not limited to", unless expressly specified otherwise.

Similarly, it is to be noticed that the term "coupled", also used in the claims, should not be interpreted as being limitative to direct connections only. Thus, the scope of the expression "a device A coupled to a device B" should not be limited to devices or systems wherein an output of device A is directly connected to an input of device B. It means that there exists a path between an output of A and an input of B which may be a path including other devices or means.

The enumerated listing of items does not imply that any or all of the items are mutually exclusive, unless expressly specified otherwise. The terms "a", "an" and "the" mean "one or more", unless expressly specified otherwise.

Elements of the invention that are in communication with each other need not be in continuous communication with each other, unless expressly specified otherwise. In addition, elements of the invention that are in communication with each other may communicate directly or indirectly through one or more other elements or other intermediaries.

One skilled in the art will appreciate that the present invention can be practiced by other than the above-described embodiments, which are presented in this description for purposes of illustration and not of limitation. The specification and drawings are not intended to limit the exclusionary scope of this patent document. It is noted that various equivalents for the particular embodiments discussed in this description may practice the invention as well. That is, while the present invention has been described in conjunction with specific embodiments, it is evident that any alternatives, modifications, permutations and variations will become apparent to those of ordinary skill in the art in light of the foregoing description. Accordingly, it is intended that the present invention embrace all such alternatives, modifications and variations as fall within the scope of the appended claims. The fact that a product, process or method exhibits differences from one or more of the above-described exemplary embodiments does not mean that the product or process is outside the scope (literal scope and/or other legally-recognized scope) of the following claims.

What is claimed is:

1. A light system, comprising:
 a housing including one or more LED lights, a power supply comprising a dynamo, a mode switching circuit, and a preset switch;
 an appliance, wherein the housing is removably attached to a rotatable element of the appliance;
 wherein the dynamo generates power to the LED lights by the application of rotational energy generated by the rotatable element of the appliance; and
 wherein the LED lights emit light at a wavelength between 200-280 nm, wherein wavelength selection is operable by the preset switch.

2. The light system of claim 1, wherein the power supply comprises a rechargeable battery.

3. The light system of claim 1, wherein the LED lights are disposed in at least on LED light strip.

4. The system of claim 1, wherein the housing includes a magnet for attaching the housing to the inside of the appliance.

5. The system of claim 1, wherein the housing includes one or more suction cups for attaching the housing to the inside of the appliance.

6. The light system of claim 1, wherein the LED lights are controlled by an external computing device.

7. The light system of claim 1, wherein the LED lights are controlled by a software application by a Bluetooth connection.

8. A method for disinfecting an appliance, comprising:
 a. Providing a light system comprising a housing including one or more LED lights, a power supply comprising a dynamo, a mode switching circuit, and a preset switch, wherein the LED lights are configured to emit light at a wavelength between 200-280 nm, wherein wavelength selection is operable by the preset switch;

b. Removably attaching the housing to a rotatable element of the appliance, wherein rotation of the rotatably element of the appliance rotates the dynamo to generate power to the LED lights;

c. Activating the light system by way of the mode switching circuit;

d. Allowing the LED lights to emit light for a predetermine period of disinfection.

9. The method of claim 8, wherein the power supply comprises a rechargeable battery.

10. The method of claim 8, wherein the LED lights are disposed in at least on LED light strip.

11. The method of claim 8, wherein the housing includes a magnet for attaching the housing to the inside of the appliance.

12. The method of claim 8, wherein the housing includes one or more suction cups for attaching the housing to the inside of the appliance.

13. The method of claim 8, wherein the light system is removably attached to the inside of the appliance.

14. The method of claim 8, wherein the LED lights are controlled by an external computing device.

15. The method of claim 8, wherein the LED lights are controlled by a software application by a Bluetooth connection.

\* \* \* \* \*